United States Patent [19]

Seebeck et al.

[11] 4,329,433

[45] * May 11, 1982

[54] PROCESS FOR CONTINUOUS FERMENTATION

[75] Inventors: Dietrich Seebeck, Meerbusch; Jens A. Schildmann, Partenheim; Reinhard Weisrock, Neider-Olm; Julius Koch, Eltville, all of Fed. Rep. of Germany

[73] Assignee: Peter Eckes, Nieder-Olm, Fed. Rep. of Germany

[ * ] Notice: The portion of the term of this patent subsequent to Nov. 11, 1997, has been disclaimed.

[21] Appl. No.: 128,336

[22] Filed: Mar. 7, 1980

Related U.S. Application Data

[63] Continuation-in-part of Ser. No. 960,893, Nov. 15, 1978, Pat. No. 4,233,407, Continuation-in-part of Ser. No. 957,585, Nov. 3, 1978, abandoned, Continuation-in-part of Ser. No. 876,822, Feb. 10, 1978, abandoned.

[30] Foreign Application Priority Data

Feb. 17, 1977 [DE] Fed. Rep. of Germany ....... 2706831

[51] Int. Cl.³ .................. C12C 11/14; C12G 1/00; C12N 1/18; C12M 1/12
[52] U.S. Cl. ................................ 435/255; 99/276; 426/11; 426/15; 426/16; 426/60; 426/474; 435/256; 435/311; 435/313; 435/316; 435/813
[58] Field of Search .............. 426/15, 16, 11, 474, 426/477, 60; 435/813, 311, 313, 316, 255, 171; 99/276

[56] References Cited

U.S. PATENT DOCUMENTS

| 3,173,793 | 3/1965 | Shore et al. ............................ 426/16 |
| 3,575,813 | 4/1971 | Rothmayr ....................... 435/313 X |
| 4,009,286 | 2/1977 | Moll et al. ......................... 426/16 X |
| 4,233,407 | 11/1980 | Seebeck et al. .................. 426/15 X |

OTHER PUBLICATIONS

Hind, H. L., Brewing Science and Practice, vol. II, Chapman & Hall, Ltd., London, 1950, (pp. 796–803, 839–840), TP570, H55c, 2.

Amerine et al., The Technology of Wine Making, 3rd Ed., The Avi Publ. Co., Inc., Westport, Conn. 1972, (pp. 242–264, 337, 338, 475–479), TP548, A48.

*Primary Examiner*—David M. Naff
*Attorney, Agent, or Firm*—Sprung, Felfe, Horn, Lynch & Kramer

[57] ABSTRACT

Continuous fermentation of solutions such as grape juice with wine yeast is carried out in a tower under sterile conditions. In the process, a tower with an enlarged upper end section is sterilized with steam followed by introducing sterile gas into the tower to maintain a positive pressure of sterilized gas therein, then continuously introducing a fermentable solution into the lower end of the tower, fermenting the solution while introducing a stream of bubbles of sterile gas to agitate the solution, continuously removing fermentation products from the upper end section of the tower, separating yeast from the products and reintroducing the yeast into the lower end of the tower. Before fermentation of the solution, yeast may be cultured under aerobic conditions and when the desired yeast concentration is reached, the solution to be fermented is introduced and fermented under anaerobic conditions.

5 Claims, 3 Drawing Figures

PROCESS FOR CONTINUOUS FERMENTATION

This application is a continuation-in-part application of application Ser. No. 960,893 filed Nov. 15, 1978, now U.S. Pat. No. 4,233,407, application Ser. No. 957,585 filed Nov. 3, 1978 (now abandoned) and application Ser. No. 876,822 filed Feb. 10, 1978 (now abandoned).

BACKGROUND OF THE INVENTION

The invention relates to a process for the continuous fermentation of solutions, especially of grape juice.

Processes are known in the brewing and wine industry for continuously fermenting beer wort or grape juice, in which the unfermented wort or the grape juice of the grape mash is fed continuously to a fermentation vat.

A process for continuously fermenting solutions to yield products of fermentation or microorganisms is known from the Austrian Pat. No. 155,464. In this process, the fermentation takes place in one or more double-chamber receptacles, connected in series. The unfermented mash is introduced into one chamber and, while air is blown in and a suspension is maintained, is conducted towards the top thereof, where it can flow over into the second chamber of the receptacle and sink again to the bottom. A settling chamber is connected to the double-chamber receptacle, in which the fermented mash can come to rest, so that the microorganisms are concentrated under the influence of gravity in a portion of the exhausted fermentation liquor. Since the lower part of this settling chamber is in open connection with the lower end of the double-chamber receptacle, the yeast can again enter the double-chamber receptacle of the fermentation zone from below.

In addition, a process is known from the German Pat. No. 1,209,088, which comprises a hollow slender fermentation tower for beer brewing which has inlets at its lower end for unfermented wort and for air and which is connected at its upper end over an overflow with a product-discharge line, which in turn is connected with a yeast settling chamber. The fermentation tower is connected at its upper end with a vent, through which carbon dioxide can escape.

Concerning to the German Pat. No. 1,207,324, the process therein uses a tower-fermenter which is equipped with perforated distribution elements over its length which ensure a uniform distribution of the yeast in the wort or the mash.

A further development is reported in the German Pat. No. 1,322,793 where in addition it is proposed to install a pulsation unit to ensure a good distribution of the yeast.

U.S. Pat. No. 3,575,813 describes a continuous fermentation process where, in a fermentation tower, perforated bell-shaped plates are fixed to attain a good distribution of the yeast. The fermentation tower is fed from the top.

A fermentation unit equipped with diagonal arranged perforated baffles which turn the rising fermentation gases to realize a mixing effect of the reactants is known from the U.S. Pat. No. 3,413,124.

U.S. Pat. No. 4,009,286 discloses a wort fermentation with immobilized yeast and following enzymation under sterile conditions. To attain a continuously running fermentation it is necessary to install at least two reaction units, otherwise the system only allows batchwise fermentation.

U.S. Pat. No. 3,234,026 proposes a continuously running wort fermentation by the installing of some agitator equipped vessels in one line.

U.S. Pat. No. 2,967,107 describes a fermentation system wherein some fermentation reactors equipped with special agitators are installed in one line.

With respect to U.S. Pat. No. 1,884,272 a system for culturing yeast in vats connected in series is described.

These previously known processes suffer from the common disadvantage that they represent a more or less open system, from which undesirable microorganisms, such as, for example, bacteria, cannot be entirely excluded, and thus changes may occur that could result in spoiling the products of the fermentation process, so that the suitability and the efficiency of these processes leave much to be desired.

SUMMARY OF THE INVENTION

The present invention relates to a process for culturing yeast under sterile aerobic conditions, especially a flocculent wine yeast, with following continuous fermentation of fruit juice, e.g. grape juice, in one tower-fermenter under sterile anaerobic conditions over more than 12 months. For thus long fermentation period it is only necessary to culture the yeast once.

The invention makes it possible to provide optimum conditions in one tower-fermenter as well for culturing yeast by using sintered candles for distribution of injected sterile air for getting aerobic conditions as for homogeneously distribution of the yeast by injecting inert gases over sintered candles to get the greatest possible fermentation activity (with the smallest losses of nutrient and yeast). In addition, the present process is continuous, time-saving and can be readily automated.

The invention provides a process for the continuous culturing of yeast, especially of wine yeast, for fermenting solutions and for recovering fermentation products while continuously feeding in fermentable solutions and carrying away fermentation products, wherein, before the actual fermentation of the juice, the yeast is cultured in a fermentation tower under aerobic conditions without microbiological contamination and with an enriched sterile nutrient solution especially prepared for the culture of yeast.

In a preferred embodiment of the process, a sterile nutrient solution, enriched with nutrients for the culture of yeast, is dosed continuously and under aerobic conditions into the lower region of a sterilized fermentation tower that is inoculated with the yeast, whereby the amount of nutrient solution and of air introduced is increased continuously as a function of the concentration of the yeast; the suspension of yeast rising in the fermentation tower in the nutrient solution is withdrawn continuously from the upper region of the fermentation tower, the yeast is separated off and introduced once again from below into the fermentation tower; and, on attaining the desired concentration of yeast, the fermentation is allowed to proceed by interrupting the air flow and introducing a solution of the desired juice strength.

The aerobic conditions are achieved, in accordance with the invention, by blowing fine bubbles of sterilized air into the fermentation tower from below. The air can also be blown in at various points, distributed over the height of the tower, for which purpose sintered candles are preferably used.

Grape juice or a concentrated grape juice, or other fruit juice, such as apple juice, can be used as a nutrient solution for the culture of the yeast which is brought to a sugar concentration suitable for yeast culturing by dilution with water and treated with ammonium salts as nutrient for the yeast which is to be propagated.

On the other hand, nutrient solution is continuously introduced into the fermentation tower, and on the other, the spent juice, with the yeast suspended therein, is withdrawn. The yeast is separated by a suitable procedure from the nutrient liquid and from the gases that are withdrawn with the liquid. A hydro-cyclone may, for example be used for this purpose. The separated yeast is then again introduced into the fermentation tower from below under sterile conditions with the help of a pump, preferably an eccentric screw conveyor.

In a preferred mode of carrying out the inventive process, the juice concentrate used as a nutrient solution, is diluted with water, treated with a sufficient amount of suitable nutrients and, via a dosing pump with heating and cooling facilities, is dosed continuously, in sterile form and with constant aeration, into a fermentation tower that is inoculated with yeast. With increasing yeast-cell concentration in the nutrient solution, both the amount of nutrient solution introduced and the amount of air blown in are increased. In order to ensure that the greatest possible amount of oxygen is dissolved in the juice, the sterile air is blown, in the form of fine bubbles, into the nutrient solution through several sintered candles, which are distributed over the height of the fermentation tower. At the same time, the flow of air provides adequate turbulence and thereby assures the homogeneity of the substrate so that the same reproducing conditions are available essentially to all the yeast cells. Through the continuous operation of the process, the contents of the fermentation tower rise to a certain level that is limited by an overflow pipe. A pipe connected to the overflow pipe connects to a hydrocyclone that separates the yeast from the gases that are carried along and from the fermented solution. The separated yeast is returned to the fermentation tower with the help of an eccentric screw conveyor and again subjected to the culturing process. The culturing process is ended when the yeast reaches the desired concentration. Subsequently, it is possible to switch over immediately and, if desired, automatically, to a continuous fermentation, without having to undertake any changes in the equipment.

A very good nutrient utilization and a rapid yeast reproduction is ensured by making the nutrient available continuously at an optimum level and under aerobic culturing conditions.

In the fermentation process according to the invention, the supply of sterilized air is cut off through closing of the appropriate vents and carbon dioxide is substituted, e.g., at a rate of 10 grams of carbon dioxide per hour per liter of fermentation medium. The carbon dioxide can be sterilized over a membrane filter and is introduced into the tower via sintered candles. The supply of carbon dioxide makes possible not only a rapid changeover from the aerobic to the anaerobic phase and serves to hold the yeast optimally dispersed in the tower what increases the fermentation velocity thus making possible greatly increased throughputs up to approximately 100% at the same alcohol concentration. (See the table below). Upon introduction of the $CO_2$ gas the nutrient medium is changed over to the fermentation medium. Appropriate fermentation media are fruit juice, e.g., apple juice of 12° brix or grape juice of 20° brix, optionally containing 400 ppm of diammonium hydrogen phosphate. The dose amounts are dependent on the desired degree of final fermentation, e.g., 2-3 grams per liter of residual sugar. The fermented fruit juice is withdrawn as fruit wine, e.g., apple wine or grape wine is led out of the system. The yeast which is carried along is eliminated through an appropriate separation device and is returned to the fermentation tower.

The carbon dioxide gas can be replaced by other inert gases, such as nitrogen or, preferably, by the autogenerated fermentation gas.

In a preferred embodiment of the process, the process incorporated a slender fermentation tower which has, at its lower end, inlets for the unfermented solution and for air and is, at its upper end, joined via an overflow to a product discharge line. This makes it possible to ferment, e.g., a grape juice solution, to wine over a selected period of time, using a high concentration of yeast and excluding other microorganisms.

The process of the invention desirably utilizes a steam line connected with the fermentation tower, sampling valves, an air inlet for sterile air, membrane filters in the air inlet line and in the air exhaust line and a manometer for the static control of the sterilization process.

According to a preferred embodiment of the invention, the steam line is connected via the sampling valves and a further valve with the fermentation tower.

In another preferred embodiment, the process of the invention for the continuous fermentation of fermentable solutions, especially grape juice or fruit juice, with yeast, for the production of fermentation produces, by the continuous introduction of fermentable solutions and gases into a closed fermentation tower and continuous removal of the alcoholic fermentation products, is characterized by the blowing of an inert gas into the fermentable solution to create turbulence during the fermentation process.

Preferably, 1 to 3 cubic meters and more preferably 1.5 to 1.8 cubic meters of inert gas are injected hourly into the fermentation tower or into the fermentable solution, as the case may be, for each cubic meter of fermentable solution. More advantageously, the injection of the inert gas is performed in fine bubbles by means of suitable gas diffusers, especially sintered candles.

Within the scope of the invention, the term inert gas refers to any gas that is inert in a fermentation process, such as, for example, nitrogen, carbon dioxide, or noble gas. Carbonic acid gas is preferred, it being advantageous to resort to the carbonic acid gas produced by the alcoholic fermentation.

According to a preferred embodiment of the invention, the fermentation products carried out of the fermentation tower are separated in a separator, such as hydrocyclone, into yeast, fermentation carbonic acid gas or gases containing carbon dioxide, and the fermented solution; the separated yeast is reintroduced into the fermentation tower, and the fermentation carbonic acid gas, or the gas mixture separated in the hydrocyclone and containing carbon dioxide, is partially or completely injected back into the fermentable solution by means of a blower, preferably a compressor.

It has been found advantageous to use a gas washer to clean the fermentation carbonic acid gas separated in the hydrocyclone and/or to filter it through a membrane, before injecting it into the fermentation tower.

The yeast separated from the fermentation products by means of the hydrocyclone can be recycled to the fermentation tower by means of a pump, and preferably by means of an eccentric screw conveyor.

By blowing inert gas into the fermentable solution and producing turbulence in accordance with the invention, a more intense mixing of the yeast with the fermentation substrate it accomplished, a larger active surface of the yeast is utilized for the fermentation process, and hence an increase of efficiency amounting to as much as 100% is achieved.

In a preferred embodiment of the process of the invention, the solution to be fermented is on the one hand fed continuously to the yeast-filled fermentation tower, and on the other hand the fermented solution is continuously carried out of the fermentation tower along with the fermentation products it contains. The fermentable solution can be any desired solution that is fermentable with yeast, especially fruit juice concentrates diluted with water, especially apple juice or grape juice solutions, although beer wort can also be fermented by the method of the invention.

The yeast suspended in the fermented solution, and the gases which have formed in the alcoholic fermentation and contain especially carbon dioxide, are separated in an appropriate manner, preferably by means of a hydrocyclone. The separated yeast is fed back into the bottom of the fermentation tower by means of a pump, preferably an eccentric screw conveyor.

In an especially preferred embodiment of the invention, a portion of the separated fermentation carbonic acid gas or the gases containing carbon dioxide which have been obtained from the fermentation products, is aspirated by means of a blower, preferably a compressor, and injected back into the bottom of the fermentation tower, this being done in such a manner that an intense turbulence is produced in the fermentable solution by the injected carbon dioxide.

In one embodiment of the process of the invention, the fermented solution along with the yeast suspended therein and the gases that have formed in the fermentation, are passed through an overflow tube and a conduit connected thereto into a hydrocyclone which separates the fermented solution both from the yeast suspended therein and from the entrained gases.

While the fermented solution is discharged into a collecting tank and is delivered from thence for further processing, the separated yeast is fed back into the fermentation process in the manner described.

A portion of the fermentation carbonic acid or gases containing carbon dioxide which have been separated in the hydrocyclone is aspirated from the hydrocyclone by a compressor and, for the achievement of turbulence and of an intense mixing of the yeast with the fermentable solution, is again injected in fine bubbles, preferably through a sintered metal diffuser, into the bottom of the fermentation tower. The injection of the carbon dioxide or of the carbonic acid gas produced by the fermentation is at the same time controlled such that the content of the fermentation tower, that is, the yeast and the solution being fermented, are given the appearance of a homogeneous mass. Since in the process of the invention a portion of the fermentation carbonic acid gas is recirculated, the additional carbon dioxide forming in the alcoholic fermentation must be let out of the hydrocyclone and from the system through a valve and a duct.

Additional advantages, embodiments and subject matter of the invention will appear from the further description and from the examples, in which reference is made to the appended drawings, wherein:

DETAILED DESCRIPTION OF THE PREFERRED EMBODIMENTS

Figure 1:
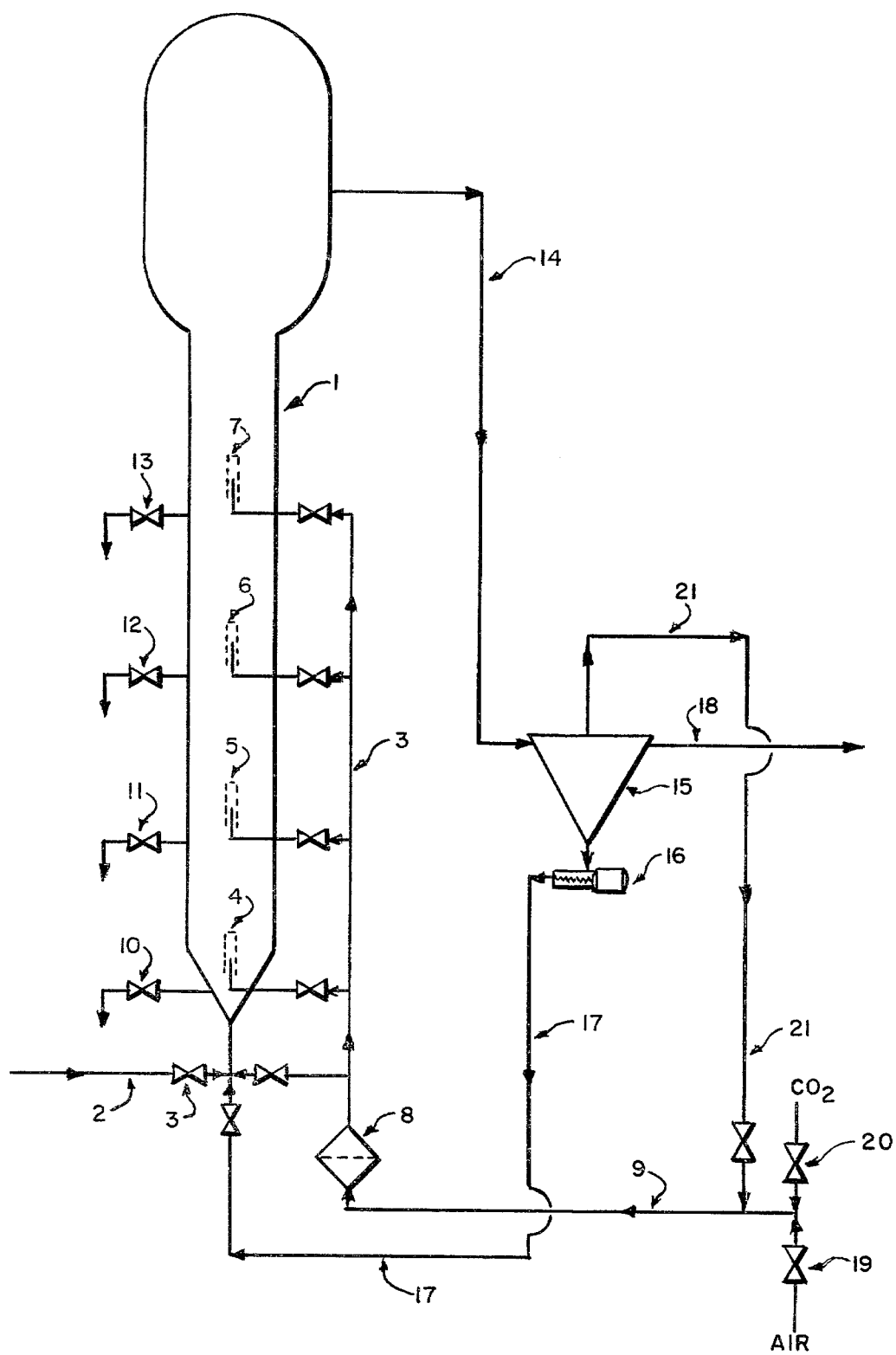
FIGS. 1-3 are diagrammatic representations and schematic flow sheets of embodiments of the process of the invention.

Referring now to FIG. 1:

Example 1 Culturing yeast

A pure culture yeast suspension ($>10^7$ cells/ml) is introduced into a sterile fermentation tower 1 through line 2 and valve 3 up to overflowing of the first sintered candle unit 4. A sterilized nutrient solution, fruit juice such as apple or grape juice, preferably of a temperature of 30° C. is continuously added immediately thereafter through line 2 and valve 3. To achieve aerobic culturing conditions, fine bubbles of sterilized air (approx. 0,5 m$^3$ per hour and candle) are blown into the culture solution through membrane filter 8, line 9 and sintered candle unit 4. The pH value of the nutrient solution of a sugar content of 10% is then adjusted by 5.5-6.0 by the addition of ammonium, 0.25% diammonium hydrogen phosphate and 0,2% diammonium hydrogen sulphate is mixed with the nutrient solution. It is well known that nutrients containing nitrogen or phosphoric acid can be of an organic nature.

Sintered candles, 5, 6 and 7 are switched on gradually as they are flooded by the continuously rising liquid level.

Under sterile conditions, samples are firstly taken daily from sterilized sampling valve 10 to determine the sugar consumption and nitrogen absorption by the yeast. Depending on this test, the amount of continuously added nutrient solution is regulated. Depending on the level of liquid, the samples then are daily taken from sampling valve 11, 12 or 13.

The contents of fermentation tower 1 rise up to the overflow pipe 14 and are lead therethrough into a separator 15. The entrained yeast is then separated in separator 15 from the overflow, spent nutrient solution and the gases which were carried along. Pump 16, e.g. an eccentric screw conveyor or a rotary pump, pumps the yeast through line 17 back into the fermentation process. The spent nutrient solution and the entrained gases are discharged from the system through line 18.

As soon as the necessary yeast concentration of approximately 125 g DW/l nutrient solution is obtained, it is changed over from aerobic culturing to anaerobic fermentation.

Example 2 Continuous fermentation

As soon as the desired yeast concentration is attained the dosing pump combination is programmed in such a way, that a reconstituted juice concentrate with a desired level is attained, whereupon the input of air is interrupted by closing valve 19. As a consequence, fermentation occurs within a short time under the influence of the yeast. During the fermentation sterile juice is continuously introduced. The fermentation solution is fruit juice, preferably apple juice of 12° brix or grape juice of 20° brix, to which was added 400 ppm diammonium hydrogen phosphate. The continuous dosage volume depends on the final degree of fermentation, e.g. 2-3 g/l rest sugar.

The fermented fruit juice, e.g. apple wine or grape wine, is then discharged continuously from the system through line 14, the separator 15 and line 18. The entrained yeast is separated in separator 15 and is returned to the tower 1 by means of a pump 16 through line 17.

The fruit juice dosage depends on the sugar content of the fed juice, the concentration of the yeast, the fermentation power of the yeast and the desired alcohol content of the end product. For attaining, e.g. 11% alcohol by volume in the fermented juice, the hourly dosage of fruit juice can be in a ratio of 1:20 to the content of the fermentation column. The yield of alcohol is about 94%, based on the stoichiometric yield.

For controlling the fermentation process, sterile samples are taken from sample valve 13. Depending on the condition of the yeast, sterile air can also be injected.

Example 3 Continuous fermentation by gas recycling

As soon as the desired yeast concentration is attained the dosing pump combination is programmed in such a way, that reconstituted juice concentrate with a desired level is attained. For changing over from aerobic culturing to anaerobic fermentation aeration is shut off by closing valve 19 and thereafter approximately 10 g $CO_2$/h/l sterilized by membrane filter 8 are added through line 9 and opening of valve 20. The $CO_2$ gas enables not only a fast changeover from the aerobic to the anaerobic phase but it also keeps the yeast homogeneously distributed within the tower. Only a homogeneously distributed yeast ensures optimum fermentation (see the Table below). The $CO_2$ gas may also be replaced by inert gases, preferably nitrogen.

The fermentation solution is fruit juice, preferably apple juice of 12° brix, to which was added 400 ppm diammonium hydrogen phosphate. The continuous dosage volume depends on the final degree of fermentation, e.g. 2-3 g/l rest sugar.

The fermented fruit juice, e.g. apple wine or grape wine, is then discharged continuously from the system through line 14, the separator 15 and line 18. The entrained yeast is separated in separator 15 and is returned to the tower by means of a pump 16 through line 17. Part of the fermentation gases, entrained through line 14 and separated in the separator 15, replaced totally the $CO_2$ gas which was injected in the initial phase of fermentation through valve 20 and is then returned through line 21 and sterilized by membrane filter 8 with the aid of a fan or blower (not shown). The continuously developing and not reused fermentation gases are discharged through line 18.

The fruit juice dosage depends on the sugar content of the fed juice, the concentration of the yeast, the fermentation power of the yeast and the desired alcohol content of the end product. For attaining, e.g. 11% alcohol by volume in the fermented juice, the hourly dosage of fruit juice can be in a ratio of 1:10 of the content of the fermentation column. The yield of alcohol is about 94%, based on the stoichiometric yield.

For controlling the fermentation process, sterile samples are taken from sample valve 13. Depending on the condition of the yeast, sterile air can also be injected.

TABLE

Shortening the contact time of fruit juice with yeast in the fermentation tower, as a function of the yeast which is homogeneously distributed through carbon dioxide aeration

| | Without $CO_2$ addition | | With 10 g $CO_2$ addition/l fermentation solution | |
|---|---|---|---|---|
| | apple juice | grape juice | apple juice | grape juice |
| Sugar before fermentation (g/l) | 110 | 190 | 110 | 190 |
| Residual sugar after fermentation (g/l) | 2-3 | 5 | 2-3 | 5 |
| Alcohol (g/l) | 52 | 90 | 52 | 90 |
| Contact period of the fermentation solution with the yeast (h) | 6 | 11 | 3 | 5-6 |

Figure 2:
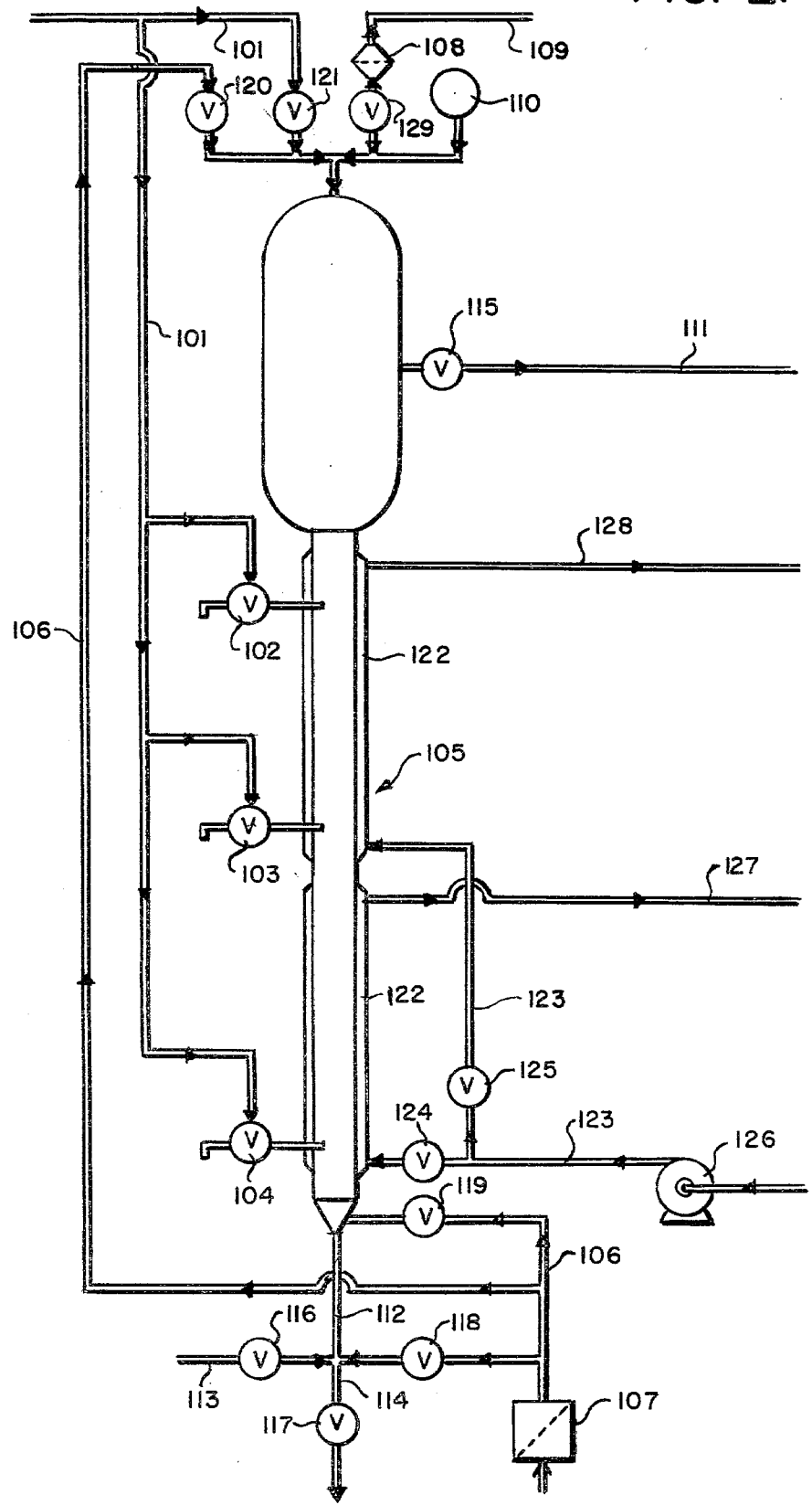

With reference to FIG. 2, the inventive process is carried out by an apparatus comprising a fermentation tower 105, which is free of components in its interior or which, if necessary, can be provided with devices, for example, sintered candles, with the help of which gas, for example air, can be introduced. A line 101, is connected with the fermentation tower 105. Via line 101, steam (for example saturated steam) can be introduced into the fermentation tower via sampling valves 102, 103 and 104 or valve 121, for the purpose of sterilization. The fermentation tower 105 is provided at its lower end and at its upper side with an air intake 106, over which sterilized air is blown into the equipment. For this purpose, the air is initially passed over membrane filter 107, which retains the undesirable germs. In exhaust line 109, a further membrane filter 108 is provided, which enables the fermentation gases to leave, but prevents undesirable microorganisms and other impurities from entering. The membrane filters 107, 108 are equipped with flter membranes, suitable for sterilizing air. The manometer 110 is used for statically monitoring the sterilization and fermentation processes and the device is operated in such a way that, especially while cooling the tower, no underpressure or vacuum arises, but there is instead at all times a slight overpressure in excess of atmospheric pressure in the equipment. Even after sterilization, this overpressure is maintained, by introducing sterile air, from the time that the equipment has been cooled to room temperature until it is inoculated with yeast.

During operation, unfermented solution or fresh grape juice is continuously introduced into the fermentation tower over line 113, valve 116 and line 112, in which solution or juice, after inoculation with yeast, the yeast is cultured and fermentation takes place, whereby, because of the continuous addition of fresh juice, the product flows off via the overflow (not shown), through valve 115 and into product discharge line 111. There is a certain calming of the yeast suspension in the enlarged, upper region of the fermentation tower 105, so that only a slight amount of yeast is drawn off with the product from the fermentation tower. Finally, the fermentation tower can be emptied over lines 112 and 114 as well as valve 117. The added air, sterilized with the help of membrane filter 107, can be introduced via valve 118 and line 112, via line 106 and valve 120 and via line 106 and valve 119.

Finally, the fermentation tower 105 is equipped with a heating and cooling mantle 122 (shown in two parts) that, via pump 126, supplies line 123 and valves 124 and 125 with the heating or cooling medium, that flows off over lines 127 and 128. With the help of this heating and cooling mantle, the fermentation tower is brought to the desired temperature and, during the fermentation, maintained at the optimum fermentation temperature.

To monitor the fermentation process, samples for checking the fermentation, the yeast, etc., can periodically be taken via sampling valves 102, 103 and 104 and analyzed. By automating the sampling and the analysis, it is also possible to control the fermentation process automatically.

Before and after taking samples, the sampling valves intended for this purpose are steamed in order to clean and sterilize them. Steam, introduced through line 101, is used for this purpose.

When starting up the operation of the inventive equipment, steam (saturated steam) is introduced into the equipment over line 101, whereby all valves are opened to such an extent that steam barely flows out of the equipment. At the same time, membrane filters 107 and 108 are also sterilized.

When the steaming is completed, sterilized air is blown into the fermentation tower 105 over line 106 and valves 119 and 120 or over line 106 and valve 118 and line 112. In so doing, the current of air is controlled with the help of the manometer 110 in such a way, that underpressure does not develop in the tower during cooling, but that instead a slight overpressure is maintained in the equipment. This overpressure is maintained even after the equipment has reached room temperature and while it is being inoculated.

Then, for culturing the yeast, unfermented nutrient solution is introduced into the fermentation tower 105 from below via line 113, valve 116 and line 112, whereby, if required for maintaining aerobic conditions, sterilized air is introduced into the equipment from below via line 106 and valve 119, which can advantageously be done with the help of sintered candles, which facilitate blowing fine bubbles of air into the fermentation tower. After the desired concentration of yeast has been attained in the fermentation tower, the fermentation process is continued continuously by constantly feeding in unfermented solution (via line 113, valve 116 and line 112) and constantly carrying away the products via valve 115 and line 111. The exhaust gases, formed during the culture, and also the carbon dioxide of the fermentation are conducted away via valve 129, the exhaust-gas line 109 and the membrane filter 108, so that a state is reached in which, though the exhaust gases escape, no harmful microorganisms can penetrate in from the external air.

Yeast cells which, together with the products, are removed from the fermentation tower via valve 115 and line 111, can be separated off and fed once again from below into the fermentation tower via line 113, valve 116 and line 112.

According to the invention, the process for fermenting solutions, especially grape juice, can be carried out continuously under sterile conditions in an extremely simple and advantageous manner, without having to fear that undesirable microorganisms will be carried in and so cause the fermenting material to be spoiled.

Example 4

Figure 3:
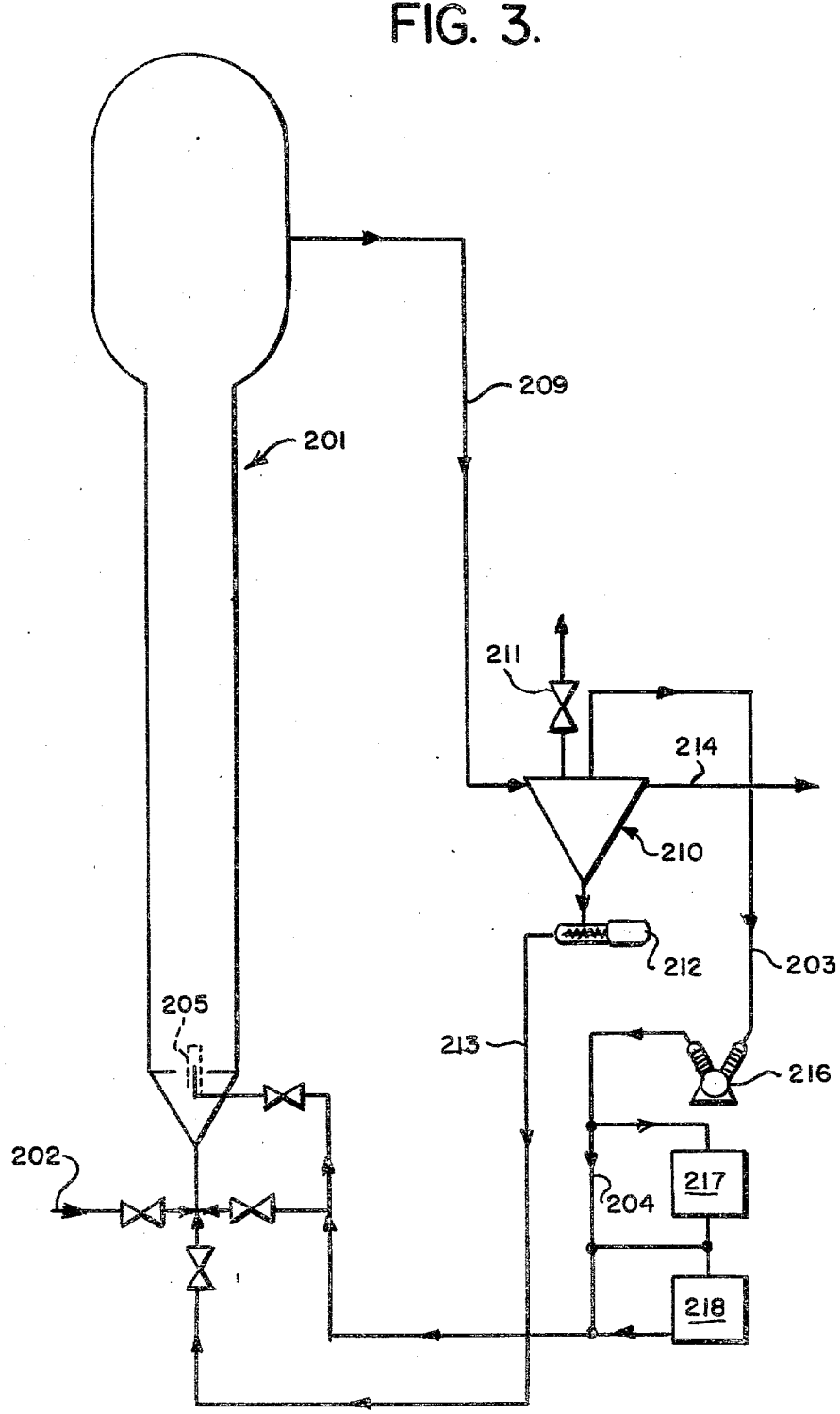

With reference to FIG. 3 the following example will serve to further explain the invention.

Fresh fermentable solution is continuously fed through a line 202 into the yeast-filled fermentation tower 201. The content level of the fermentation tower 201 rises as far as the conduit 209, which is designed as an overflow conduit and is carried by the latter to a hydrocyclone. In this hydrocyclone 210, the entrained yeast is separated from the entrained, carbon dioxide-containing gases, and from the overflowing, fermented solution, and it flows to an auger pump 212. This pump 212 delivers the yeast through conduit 213 back into the fermentation tower 201 and thus recycles it to the fermentation process.

Through a conduit 203, a portion of the fermentation carbonic acid gas is aspirated from the hydrocyclone 210 by means of a compressor 216 which then injects it back into the fermentation tower through a line 204 and one or more sintered candles 205 (only one such candle being represented diagrammatically in the drawing). If the gas washer 217 is inserted into the circuit, the purified fermentation carbonic acid gas is injected back into the fermentation tower through a sterile filter 218 (membrane filter). To achieve a sufficient turbulence and an intense mixing action, the carbon dioxide is injected into the fermentation tower, whose capacity is 10 cubic meters, at a rate of 15 to 18 cubic meters (under standard conditions) per hour. The excess carbon dioxide and carbon dioxide-containing gas is carried out of the system through a valve 211.

It will be understood that the specification and examples are illustrative but not limitative of the present invention and that embodiments within the spirit and scope of the invention will suggest themselves to those skilled in the art.

What is claimed is:

1. A process for the continuous fermentation of fermentable solutions with yeast to produce fermentation products in a closed upright slender fermentation tower having a hollow interior, a lower end, and an enlarged upper end section, comprising the steps:
   (a) sterilizing the tower by introducing into the upper and lower ends of the tower and through steam inlet means provided along the length thereof, a stream of steam;
   (b) introducing sterilized gas into the upper end of the tower through a sterile gas inlet fitted with a membrane filter and exhausting the sterilized gas through a gas exhaust fitted with a membrane filter and pressure regulating means to maintain a positive pressure of sterilized gas therein to restrain the entrance of contaminants into the tower;
   (c) continuously introducing a fermentable solution into the lower end of the tower;
   (d) fermenting the fermentable solution while agitating the fermentable solution by continuously introducing a stream of bubbles of sterile gas into the lower end of the tower through a sintered candle device;
   (e) periodically removing samples of the fermentation mixture to monitor the fermentation reaction and thereafter supplying steam to the sampling means to maintain its sterility;
   (f) continuously removing the fermentation products from the enlarged upper end section of the tower;
   (g) separating yeast cells from the products removed from the tower and reintroducing the yeast cells into the lower end of the tower.

2. Process as claimed in claim 1 wherein, 1 to 3 cubic meters of the sterilized gas are injected hourly per cubic meter of the fermentable solution.

3. Process as claimed in claim 2 wherein, 1.5 to 1.8 cubic meters of the sterilized gas are injected hourly per cubic meter of the fermentable solution.

4. Process as claimed in claim 1 wherein, said sterilized gas is injected in the form of fine bubbles into said fermentable solution.

5. Process as claimed in claim 1 wherein the sterile gas is nitrogen, or sterile air.

* * * * *